US012731254B2

(12) United States Patent
Tulsidas et al.

(10) Patent No.: US 12,731,254 B2
(45) Date of Patent: Sep. 8, 2026

(54) AI DRIVEN SYSTEM FOR X-RAY ANALYSIS OF VARIOUS PRODUCTS AND IDENTIFYING DEFECTS WITHIN

(71) Applicant: Techolution Consulting LLC, New York, NY (US)

(72) Inventors: Luv Tulsidas, New York, NY (US); Asher Williams, New York, NY (US)

(73) Assignee: Techolution Consulting LLC, New York, NY (US)

( * ) Notice: Subject to any disclaimer, the term of this patent is extended or adjusted under 35 U.S.C. 154(b) by 210 days.

(21) Appl. No.: 18/653,349

(22) Filed: May 2, 2024

(65) Prior Publication Data

US 2025/0342582 A1 Nov. 6, 2025

(51) Int. Cl.

*G06T 7/00* (2017.01)
*G06T 7/10* (2017.01)
*G16H 15/00* (2018.01)

(52) U.S. Cl.

CPC .............. *G06T 7/0012* (2013.01); *G06T 7/10* (2017.01); *G16H 15/00* (2018.01); *G06T 2207/10116* (2013.01); *G06T 2207/20081* (2013.01); *G06T 2207/20084* (2013.01)

(58) Field of Classification Search

CPC ................... G01N 23/04; G01N 23/18; G01N 2223/1016; G01N 2223/401

See application file for complete search history.

(56) References Cited

PUBLICATIONS

Ajina et al. "Revolutionizing Quality Control . . . " 2024 International Conference on Emerging Technologies in Computer Science for Interdisciplinary Applications (ICETCS), Bengaluru, India, 2024, pp. 1-6. (Year: 2024).*

* cited by examiner

*Primary Examiner* — Mark R Gaworecki

(74) *Attorney, Agent, or Firm* — Mestechkin Law Group P.C.

(57) ABSTRACT

An AI-driven system crafted for the precise X-ray analysis of a variety of objects and identifying defects with high accuracy. Specifically, the system conducts a thorough X-ray analysis of products, systematically identifying defects part by part (using a co-pilot interface) and categorizing them with precision as either pass (non-defective) or fail (defective).

In this system, through an intuitive co-pilot interface, the AI collaborates seamlessly with experts, offering detailed views of identified defects along with reference guides, enhancing the overall defect identification process. This interface fosters active participation of experts in the defect identification process, thereby elevating the system's accuracy and reliability and the system iteratively retrains the AI model via this interface, enhancing its capabilities to surpass human precision and effectiveness.

15 Claims, 1 Drawing Sheet

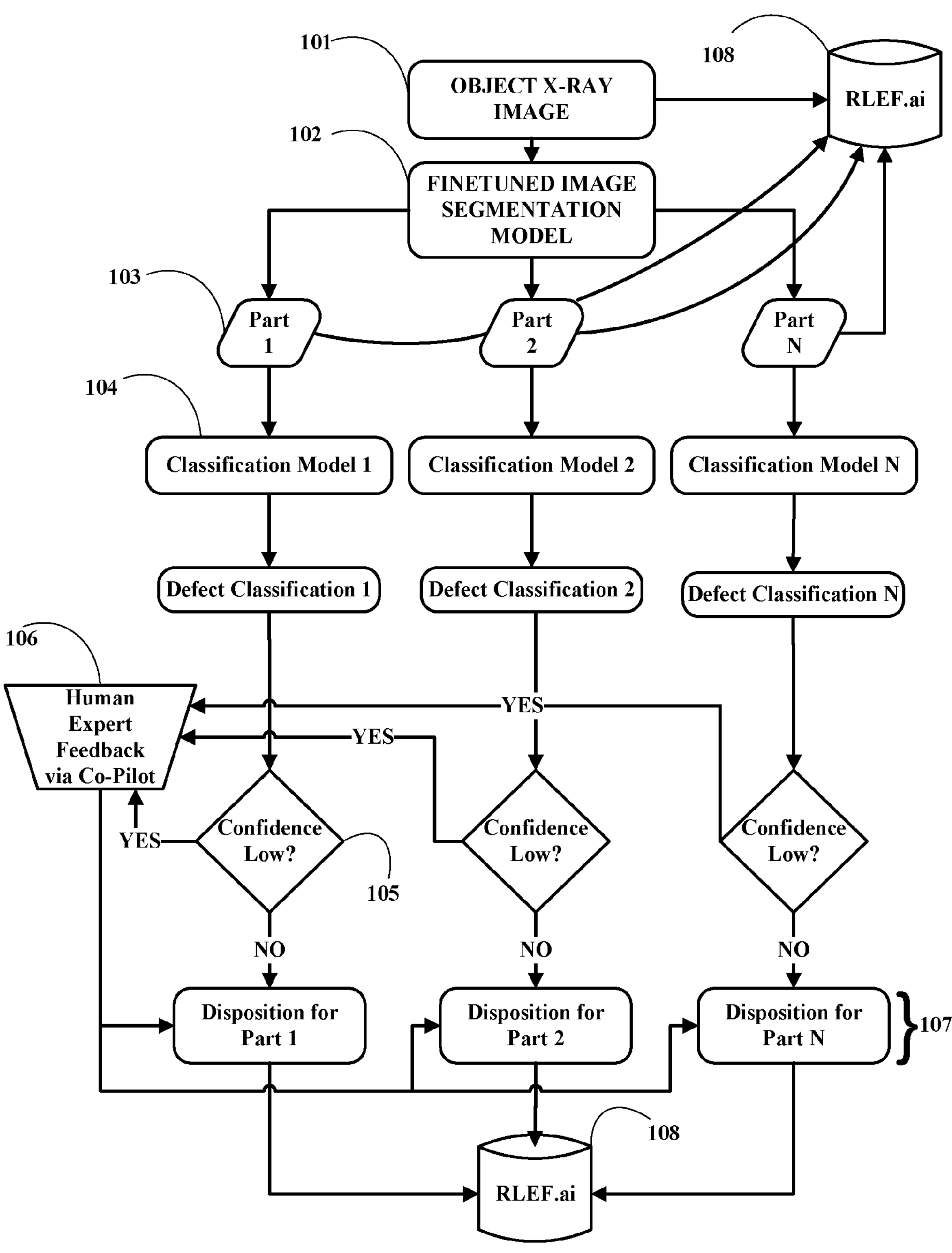

101
OBJECT X-RAY IMAGE
108
RLEF.ai
102
FINETUNED IMAGE SEGMENTATION MODEL
103
Part 1
Part 2
Part N
104
Classification Model 1
Classification Model 2
Classification Model N
Defect Classification 1
Defect Classification 2
Defect Classification N
106
Human Expert Feedback via Co-Pilot
YES
YES
YES
Confidence Low?
Confidence Low?
Confidence Low?
105
NO
NO
NO
Disposition for Part 1
Disposition for Part 2
Disposition for Part N
107
108
RLEF.ai

AI DRIVEN SYSTEM FOR X-RAY ANALYSIS OF VARIOUS PRODUCTS AND IDENTIFYING DEFECTS WITHIN

TECHNICAL FIELD OF THE INVENTION

The present invention generally relates to the field of quality control and inspection systems. Specifically, the present invention relates to an AI-driven system for conducting precise X-ray analysis of images across a diverse range of products, identifying anomalies (defects) in real time and categorizing them as defective or non-defective.

BACKGROUND OF THE INVENTION

Quality control and inspection systems play a crucial role in modern manufacturing processes, serving as the first line of defense against defects and flaws that may compromise product integrity.

Traditional quality control methods often rely on manual inspection, which is time-consuming, labor-intensive, and prone to human errors. As a result, there is a growing demand for automated inspection solutions that offer greater accuracy, efficiency, and reliability.

X-ray analysis is considered as a powerful method for inspecting the internal structures of objects. By generating high-resolution images that penetrate surfaces and reveal hidden defects, X-ray technology has become indispensable in industries such as manufacturing, aerospace, automotive, and electronics.

However, conventional X-ray inspection techniques are limited by their ability to efficiently and accurately identify defects, especially in complex product structures. One significant limitation is the lack of precision and speed inherent in manual inspection processes. Human operators may struggle to accurately interpret X-ray images, leading to inconsistencies and delays in defect identification.

Particularly prevalent within the medical imaging industry, existing systems lack automated segmentation techniques, dynamic learning capabilities, and fail to establish a collaborative interface between experts and AI systems.

The existing systems have several drawbacks.

Firstly, these systems suffer from inefficiencies and errors due to their dependence on human intervention. This reliance prolongs processing times and diminishes overall system precision, thereby hampering the effectiveness of defect identification processes.

Secondly, there is a lack of detailed part by part identification of defects in the current solution. This limitation results in increased error rates and reduces the precision of the identification process, ultimately compromising the accuracy of defect detection.

Thirdly, the absence of explicit features, such as sub-portion segmentation and dynamic learning, severely hinders the capability of existing defect identification systems. Without these features, the systems lack the sophistication needed to accurately and efficiently detect defects, leading to suboptimal performance.

Lastly, the lack of a collaborative interface limits the adaptability of existing solutions to diverse product structures. Without a means for seamless interaction between human experts and the AI system, the effectiveness of defect identification processes is constrained, hindering the system's ability to address complex manufacturing challenges.

Most of the current defect identification systems exhibit limited flexibility in adapting to a wide range of product structures. This constraint arises from the systems' reliance on fixed features and methodologies, which fail to accommodate the diverse characteristics of different products, thereby limiting their applicability across various industries.

Furthermore, these systems struggle to accurately categorize defects as pass or fail. The absence of explicit features further complicates this task, impacting the system's ability to provide precise defect categorization. As a result, manufacturers may encounter difficulties in effectively addressing identified defects and implementing corrective actions.

These shortcomings significantly impede the efficiency and accuracy of defect identification processes.

To overcome these challenges and advance the state of the art, there is a pressing need for an AI-driven system specifically designed for conducting precise X-ray analysis across a diverse range of products.

By harnessing the capabilities of AI technology, the system aims to enhance defect detection accuracy, streamline inspection processes, and improve overall product quality.

SUMMARY OF THE INVENTION

The present invention is directed to a system for conducting a thorough X-ray analysis of the products, identifying defects part by part (using a co-pilot interface) and categorizing them with precision as either pass (non-defective) or fail (defective).

In an embodiment of the present invention, the system includes a sub-portion segmentation module, multiple AI classification models, a dynamic learning mechanism, a collaborative co-pilot interface, and a real-time feedback loop.

In a preferred embodiment of the present invention, the system for X-ray analysis and defect identification, comprises X-ray imaging equipment capable of acquiring images of products; a cloud server hosting a sophisticated computer vision algorithm responsible for processing X-ray images of products; a sub-portion segmentation module for facilitating the segmentation of product images into distinct parts; AI classification models to classify and categorize defects present in each segmented part of the product and assign confidence scores, ranging between 0 and 1, a dynamic learning module configured to continuously refine the accuracy of defect identification through iterative improvement of the AI model; a co-pilot interface enabling real-time collaboration between human experts and the AI system, and a feedback loop facilitating the seamless incorporation of real-time feedback from human experts.

In another embodiment of the present invention, co-pilot interface enables the AI model to collaborate seamlessly with experts, offering detailed views of identified defects along with reference guides, enhancing the overall defect identification process.

In yet another embodiment of the present invention, higher confidence score indicates that the AI model is more confident in its classification of defects and a low confidence score suggests that the AI is less certain about its predictions.

It should be noted that while the present invention has been described with reference to one or more products, it is not limited to any particular product, in fact the one or more products may be heterogenous. Additionally, various modifications and alterations to the system and method may be possible without departing from the scope of the invention.

BRIEF DESCRIPTION OF THE DRAWINGS

The foregoing summary, as well as the following detailed description of various embodiments, is better understood when read in conjunction with the drawings provided herein. For the purposes of illustration, the drawings disclose subject matter which is not limited to the specific methods and instrumentalities disclosed. Further, the advantages and features of the present disclosure will better understood with reference to the following detailed description and claims taken in conjunction with the accompanying drawing, wherein like elements are identified with like symbols, and in which:

FIG. 1 illustrates the block diagram of the present system architecture, according to an embodiment of the present invention.

DETAILED DESCRIPTION OF THE INVENTION

The following description includes the preferred best mode of one embodiment of the present invention. It will be clear from this description of the invention that the invention is not limited to these illustrated embodiments but that the invention also includes a variety of modifications and embodiments thereto. Therefore, the present description should be seen as illustrative and not limiting. While the invention is susceptible to various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

In any embodiment described herein, the open-ended terms "comprising," "comprises," and the like (which are synonymous with "including," "having" and "characterized by") may be replaced by the respective partially closed phrases "consisting essentially of," consists essentially of," and the like or the respective closed phrases "consisting of," "consists of, the like.

As used herein, the singular forms "a," "an," and "the" designate both the singular and the plural, unless expressly stated to designate the singular only.

Further, the use of terms "first", "second", and "third", and the like, herein do not denote any order, quantity, or importance, but rather are used to distinguish one element from another.

The term "confidence score" is a numerical representation of the AI model's certainty or confidence in its predictions. It typically ranges from 0 to 1, where 0 indicates low confidence and 1 indicates high confidence.

The present invention is directed to an AI-driven system tailored for conducting X-ray analysis and defect identification within various products. The invention introduces a comprehensive system that integrates AI technology with human expertise, thereby enhancing the precision and efficiency of defect identification.

The system comprises an X-ray imaging equipment, a cloud server, a sub-portion segmentation module seamlessly integrated with the X-ray imaging equipment, plurality of AI classification models, a dynamic learning module, a co-pilot interface tightly integrated with the dynamic learning module and a feedback loop integrated into the system.

FIG. 1 illustrates a block diagram of the AI system, comprising the below steps:

Step 101: Receiving an X-Ray Image

In this step, X-ray images are obtained from the X-ray imaging equipment, capturing detailed internal structures of the products for inspection. The images are of sufficient quality and resolution to facilitate accurate analysis.

Step 102: Image Segmentation

In this step, a pre-trained Image Segmentation Model is used to partition the X-ray image into distinct regions corresponding to individual parts of the product. Furthermore, advanced computer vision techniques such as semantic segmentation or instance segmentation are employed to accurately delineate each part within the image.

Semantic segmentation generally refers to a computer vision task that involves partitioning an image into multiple segments or regions and assigning a semantic label to each segment. Unlike object detection, which identifies and delineates individual objects within an image, semantic segmentation aims to classify each pixel in the image into predefined categories or classes, without distinguishing between different instances of the same class. The goal of semantic segmentation is to understand the scene at the pixel level, enabling computers to comprehend the spatial layout and semantic meaning of objects within an image. Semantic segmentation may be performed using a deep learning technique. For example, a convolutional neural network. A convolutional neural network may learn to map input images to output segmentation maps, where each pixel is assigned a class label.

Similarly, instance segmentation is a computer vision task that involves identifying and delineating individual objects within an image. Unlike semantic segmentation, which classifies each pixel in an image into pre-defined categories (e.g., person, car, tree), instance segmentation goes a step further by not only labeling each pixel but also distinguishing between different instances of the same class. In other words, instance segmentation assigns a unique label to each object instance in the image. The output of an instance segmentation model is a set of masks, where each mask corresponds to a specific object instance. These masks precisely outline the boundaries of each object instance, allowing for accurate localization and separation of objects even when they overlap or are close together in the image. Instance segmentation is performed using deep learning techniques, for example, one deep learning technique is a convolutional neural network.

Step 103: Handling Identified Parts

1. Cropping and Storage:

The original X-ray image obtained is cropped to extract each segmented part, creating separate cropped images for further analysis. Thereafter the cropped images are stored in the system along with their corresponding labels in a structured format.

2. Storing in Database

The system may save cropped image parts in a dedicated database or repository, to facilitate future training and reference. In this step storing the images ensures proper organization and metadata tagging for easy retrieval and analysis.

3. Handling Missing Parts

In this step, the system identifies any expected parts that are not detected in the X-ray image Step 101. The missing parts are flagged for further investigation, as they may indicate defects or anomalies in the product.

Step 104: Part Classification

In this step, each of the cropped image is assigned to a specific fine-tuned Image Classification Model designed to classify defects. The classification models using labeled data are trained to differentiate between defective and non-defective parts based on visual cues extracted from the X-ray images.

Step 105: Confidence Evaluation

In this step, the confidence score/level associated with each classification decision made by the Image Classification Model is evaluated. The system uses statistical metrics or probability scores to quantify the reliability and certainty of the model's predictions.

Step 106: Decision Validation

In Step 106, if the confidence score falls below a predetermined threshold, the specific part of the product is escalated to a human expert for manual review. The co-pilot interface is leveraged to facilitate seamless collaboration and communication between the AI system and human experts.

If the confidence score exceeds the threshold, the system proceeds to Step 107 without human intervention, optimizing efficiency in decision-making.

Step 107: Saving Decisions

The final decision for each part analyzed is recorded, including its classification outcome (defective or non-defective) and associated confidence score. Comprehensive reports can be generated summarizing the inspection results, highlighting detected defects and their locations.

Step 108: Data Management

In this step, the decisions, dispositions, and relevant metadata are saved in the designated database or repository.

Central to the system is the X-ray imaging equipment capable of capturing detailed images of products under examination. These images serve as the foundation for subsequent analysis, enabling the system to identify defects with precision.

The cloud-based server hosts a sophisticated computer vision algorithm responsible for processing the acquired X-ray images. Leveraging state-of-the-art machine learning techniques, this algorithm dissects the intricate details of product images, facilitating the identification and classification of defects.

The cloud server serves as a hub of data storage, analysis, and decision-making based on past experiences and domain expert knowledge and encompassing physical/non-physical attributes derived from the surrounding environment.

Furthermore, the sub-portion segmentation module partitions the product images into distinct segments, enabling analysis of individual parts of the analyzed products. Through this segmentation process, the system gains insights into the structural integrity of each component, laying the groundwork for precise defect identification.

The segmented product parts and extracted features serve as input to the AI classification models responsible for defect identification. The multiple AI classification models are trained to categorize defects within segmented product parts. These models assign confidence scores to their classifications. These scores indicate the level of certainty or confidence that the model has in its defect identification.

Confidence scores typically range from 0 to 1, where 0 represents low confidence (uncertain classification) and 1 represents high confidence (certain classification).

A higher confidence score indicates that the AI model is more confident in its classification of defects and a low confidence score suggests that the AI is less certain about its predictions.

To further enhance the accuracy, the dynamic learning module continuously refines the AI models through iterative improvements, adapting to evolving patterns and enhancing overall performance of the system.

The collaborative co-pilot interface is an integral part of the system. It's a platform that bridges the gap between AI technology and human expertise. This interface facilitates real-time collaboration between human experts and the AI system, empowering experts to validate the confidence scores assigned to defect classifications.

Through this interface, experts can validate defect classifications, provide feedback, and guide the system's decision-making process. The interface offers detailed views of identified defects along with reference guides, enhancing the overall defect identification process. By fostering active participation of experts, the interface elevates the system's accuracy and reliability.

Additionally, it enables seamless feedback and correction loops, ensuring the integrity and accuracy of the defect identification process.

The feedback loop is integrated in the system architecture and enables seamless incorporation of human feedback into the learning process. This loop ensures that the system continually learns and improves from expert input, refining its defect identification capabilities with each iteration.

Furthermore, the system's capabilities extend beyond individual defect identification, supporting quality control checks for multiple products simultaneously.

A database in the system facilitates the storage of product details and enables dynamic adaptation to various product types through a streamlined onboarding process. This database facilitates efficient data storage, retrieval, and analysis, enabling insights into defect trends, performance metrics, and quality control measures.

A user interface provides intuitive displays of defect categories within products, categorized as either pass (non-defective) or fail (defective). The user interface may incorporate interactive features that allow users to explore defect categories within products in more detail.

For instance, users may be able to zoom in on specific areas of product images to get a closer look at detected defects, or hover over highlighted regions to view additional information about the type and severity of defects.

The interface provides real-time updates to ensure that users have access to the information regarding defect categories within products. As new defects are detected or existing defects are reclassified, the interface automatically reflects these changes, keeping users informed and up-to-date.

This interface supports a variety of modalities, including web-based and mobile-based interactions, ensuring accessibility across diverse user preferences.

The system can be implemented in various industrial settings, including manufacturing, aerospace, automotive, electronics, and healthcare.

Depending on the specific requirements of each application, the system can be customized and adapted to suit different product types, defect categories, and inspection workflows.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub combinations of the various features described herein above as well as variations and modifications thereof, which would occur to persons skilled in the art upon reading the foregoing description.

The invention claimed is:

1. An artificial intelligence system for X-ray analysis and defect identification, comprising:

an x-ray imaging equipment capable of acquiring one or more x-ray images of one or more products;

a cloud server hosting a computer vision algorithm responsible for processing the one or more x-ray images of the one or more products;

a sub-portion segmentation module seamlessly integrated with the x-ray imaging equipment segmenting the one or more x-ray images into one or more distinct parts;

a plurality of artificial intelligence classification models trained to classify and categorize one or more defects present in each of the one or more distinct parts, wherein the plurality of models assign one or more confidence scores, the confidence scores ranging between 0 and 1, to each classification;

a dynamic learning module configured to continuously refine defect classification through iterative improvement of the plurality of artificial intelligence classification models;

a co-pilot interface operatively coupled with the dynamic learning module, enabling real-time collaboration between one or more human experts and the artificial intelligence system, wherein the co-pilot interface allows the one or more human experts to validate the one or more confidence scores of each distinct part based on a category of identified defect; and a feedback loop integrated into the x-ray imaging equipment, facilitating real-time feedback from one or more human experts.

2. The system of claim 1, wherein a higher confidence score indicates that the one or more artificial intelligence classification models is more confident in defect classification.

3. The system of claim 1, wherein a lower confidence score suggests that the one or more artificial intelligence classification models is less certain in defect classification.

4. The system of claim 1, wherein the one or more defects are categorized as pass (non-defective) or fail (defective).

5. The system of claim 1, comprising a computer-readable storage medium containing instructions for performing x-ray analysis and defect identification.

6. The system of claim 1, a quality control check module performing quality control checks for a plurality of products simultaneously.

7. The system of claim 1, comprising a database for storing one or more product details and for dynamically adapting to a plurality of products by a one-time onboarding process.

8. The system of claim 1, comprising a user interface for displaying the one or more categorized defects within the product as pass or fail.

9. The system of claim 8, wherein the user interface is a multimodal interface.

10. The system of claim 9, wherein the multimodal interface is web based.

11. The system of claim 9, wherein the multimodal interface is a mobile based interface.

12. The system of claim 1, comprising an input/output module supporting text based data and visual data.

13. The system of claim 1, wherein the co-pilot module includes a plurality of machine learning algorithms trained to dynamically identify and rectify errors in real-time by adjusting a training data set.

14. The system of claim 1, wherein the x-ray imaging equipment detects and identifies one or more missing parts of the one or more products, the one or more products identified with one or more missing parts flagged for investigation.

15. The system of claim 1, wherein the cloud server generates a quality control report summarizing one or more inspection results, highlighting detected defects of the one or more products and a location of the detected defects.

* * * * *